(12) United States Patent
Adam et al.

(10) Patent No.: US 6,774,137 B2
(45) Date of Patent: Aug. 10, 2004

(54) OPHTHALMIC COMPOSITION

(75) Inventors: Marcia Johanna Adam, Gisikon (CH); Andrea Fetz, Wetzikon (CH); Gyorgy Lajos Kis, Triboltingen (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 10/134,795

(22) Filed: Apr. 29, 2002

(65) Prior Publication Data

US 2002/0183359 A1 Dec. 5, 2002

Related U.S. Application Data

(62) Division of application No. 09/619,349, filed on Jul. 19, 2000.

(30) Foreign Application Priority Data

Jul. 23, 1999 (EP) .............................. 99114508

(51) Int. Cl.⁷ ............................. A61K 31/445
(52) U.S. Cl. ...................... 514/324; 514/912
(58) Field of Search ................. 514/324, 912

(56) References Cited

FOREIGN PATENT DOCUMENTS

| JP | 62277323 | 12/1987 |
| WO | 99/36055 | 7/1999 |

OTHER PUBLICATIONS

Fujita et al., Rinsho Iyaku [Journal of Clinical Therapeutic and Medicines], vol. 5(4), "Clinical Efficacy and Optimal Concentration of Ketotifen Ophthalmic on Allergic Conjunctivitus and Vernal Conjunctivitus", pp. 709–721, (1989) [English translation].

Kawasaki et al., Iyakuhin Kenkyu, vol. 19(5), "Eye Irritation Study on Ketotifen Fumarate–Containing Eye Drops in Rabbits (I) Eye Irritability on Single or Frequent Topical Instillation", pp. 821–826, (1988) [English translation].

Kawasaki et al., Iyakuhin Kenkyu, vol. 19(5), "Eye Irritation Study on Ketotifen Fumarate–Containing Eye Drops in Rabbits (II) Eye Irritability on Successive Four–Week or Thirteen Week Instillations", pp. 827–838, (1988) [English translation].

Mikuni et al., Ringan [Japanese Journal of Clinical Ophthalmology], vol. 36(6), "Quantitative Therapeutic Efficacy of Ketotifen Eye Drops for Allergic Conjunctivitis", pp. 573–576, (1982) [English translation].

Mikuni et al., Rinsho Iyaku [Journal of Clinical Therapeutic and Medicines], vol. 4(12), "Evaluation of Ketotifen Ophthalmic Solution on Efficacy and Safety on Allergic Conjunctivitis and Vernal Conjunctivitis—Result on Multiclinic Open Trial—", pp. 2371–2383, (1988) [English translation].

Mikuni et al., Tokai J Exp Clin Med., vol. 9, No. 1, "A Quantitative Tear Fluids Determination of Therapeutic Efficacy for Allergic Conjunctivitis", pp. 35–41, (1984).

Nakayasu et al., Rinsho Iyaku Journal of Clinical Therapeutic and Medicines, vol. 4(12), "Safety of Ketotifen Ophthalmic Solution on Ocular External and Front Region", pp. 2357–2369, (1988) [English translation].

Partial European Search Report, Dec. 13, 1999.

*Primary Examiner*—Zohreh Fay
(74) *Attorney, Agent, or Firm*—Susan L. Hess; David E. Wildman

(57) ABSTRACT

The present invention is related to an ophthalmic composition comprising ketotifen as a pharmaceutically active agent.

13 Claims, No Drawings

OPHTHALMIC COMPOSITION

This is a divisional of application Ser. No. 09/619,349, filed Jul. 19, 2000.

This invention is directed to an ophthalmic composition comprising ketotifen as a pharmaceutically active agent.

An ophthalmic composition comprising ketotifen fumarate is already known, and already on the market. The composition of the present invention is superior compared to the known compositions in that it has a substantially lower dosage of the pharmaceutically active agent. In result said composition combines a high efficacy with a better tolerability. A further surprising advantage of the composition as disclosed herein is seen in the fact that said composition can be sterilized without any significant decomposition of the pharmaceutically active agent, or other components of the composition.

The composition of the present invention comprises a ketotifen salt, in a concentration of 0.01 to 0.04%, a non-ionic tonicity agent in an amount such that the total tonicity of the composition has an osmolarity in the range of 210 to 290 milliosmoles, optionally a preservative, acid or base for bringing the pH to weak acidity, and water.

The ketotifen salt is preferably ketotifen fumarate. The concentration of the ketotifen salt is preferably 0.03 to 0.04%. The non-ionic tonicity agent is preferably glycerol. The non-ionic tonicity agent is preferably present in an amount such that the total tonicity of the composition has an osmolarity in the range of 230 to 260 milliosmoles, more preferred 235 to 255 milliosmoles. If glycerol is used, the concentration of glycerol is preferably in the range of 1.5 to 2.5%. A preservative is present for multi-dose units, but it is routinely not present in single dose units. If a preservative is present, the preferred preservative is benzalkonium chloride. Typically the amount of the preservative is 0.005 to 0.02%, more preferred 0.01%. An acid or base is used in small amounts, such as 0.05% to 0.1%, for adjusting the pH, preferred is the use of small amounts of sodium hydroxide 1N, e.g. 0.075% of such solution. The pH of the composition is adjusted to weak acidity for optimization of the stability and tolerability, and said pH of weak acidity is understood to mean preferably a pH of 4.4 to 5.8, more preferably a pH of 5 to 5.5, and most preferably a pH of 5.3. The water present in the composition is typically water for injection.

A preferred composition of this invention comprises ketotifen fumarate, in a concentration of 0.03 to 0.04%, glycerol in a concentration of 2 to 2.5%, optionally benzalkonium chloride in an amount of 0.005 to 0.02%, sodium hydroxide, and water.

The ophthalmic composition of this invention is useful as eye drops, whether as a preserved multi dose unit, or as an unpreserved single dose unit. Said eye drops do have a high therapeutic value because they can be used for the treatment and the temporary prevention of itching of the eye due to allergic conjunctivitis, and they can be used for the treatment and prevention of signs and symptoms of seasonal allergic conjunctivitis.

Despite the low concentration of the pharmaceutically active ingredient, ketotifen fumarate, the recommended dosage is lower than for known ketotifen fumarate preparations. Thus, one drop of the composition of this invention should be applied advantageously two times per day, in contrast to 1 to 2 drops four times a day of the prior art compositions. The fact that the composition of this invention can be applied with an overall very low level of pharmaceutically active ingredient, especially ketotifen fumarate, is one of the surprising findings in the context of this invention. A further finding is that a stabilizer such as for example sodium edetate might be omitted.

Said ophthalmic composition can be manufactured by mixing the ingredients, and packaging the resulting mixture, both as known in the art. Sterilization of the composition and the primary package can be effected e.g. by gamma irradiation, by ethyleneoxide treatment, by electron beam, by autoclaving or by steam sterilization.

EXAMPLE 1

Multidose Units

| | |
|---|---|
| Ketotifen fumarate | 0.25 mg (0.025%) |
| Benzalkonium chloride | 0.10 mg (0.010%) |
| Glycerol 100% | 21.25 mg (2.125%) |
| Sodium hydroxide 1 N | about 0.75 mg (~0.075%) and |
| Water for injection ad | ad 1.0 ml |

EXAMPLE 2

Single Dose Units

| | |
|---|---|
| Ketotifen fumarate | 0.25 mg (0.025%) |
| Glycerol 100% | 21.25 mg (2.125%) |
| Sodium hydroxide 1 N | about 0.75 mg (~0.075%) and |
| Water for injection ad | ad 1.0 ml |

What is claimed:

1. A method for treating allergic conjunctivitis, comprising administering to a subject suffering from or susceptible to allergic conjunctivitis an effective amount of an ophthalmic composition comprising about 0.01 to about 0.04% by weight of a ketotifen salt, a non ionic tonicity agent in an amount such that the total tonicity of the composition has an osmolarity in the range of 210 to 290 milliosmoles, a preservative, and water, wherein the pH of the composition is between 4.4 and 5.8.

2. The method of claim 1, wherein the ketotifen salt is ketotifen fumarate.

3. The method of claim 1, wherein the concentration of the ketotifen salt is 0.03 to 0.04% by weight.

4. The method of claim 1, wherein the non-ionic tonicity agent is glycerol.

5. The method of claim 4, wherein said glycerol is present in an amount of 1.5 to 2.5% by weight.

6. The method of claim 1, wherein said preservative is benzalkonium chloride.

7. The method of claim 1, wherein said ophthalmic composition consists essentially of ketotifen fumarate in a concentration between 0.03 and 0.04% by weight, glycerol in a concentration of 2 to 2.5% by weight, benzalkonium chloride in a concentration between 0.005 and 0.02% by weight, and water.

8. The method of claim 1, wherein said ophthalmic composition is administered twice per day.

9. The method of claim 8, wherein one drop of said ophthalmic composition is administered twice per day.

10. The method of claim 3, wherein said ophthalmic composition is administered twice per day.

11. The method of claim 10, wherein one drop of said ophthalmic composition is administered twice per day.

12. The method of claim 7, wherein said ophthalmic composition is administered twice per day.

13. The method of claim 12, wherein one drop of said ophthalmic composition is administered twice per day.

* * * * *

UNITED STATES PATENT AND TRADEMARK OFFICE
CERTIFICATE OF CORRECTION

PATENT NO. : 6,774,137 B2
DATED : August 10, 2004
INVENTOR(S) : Adam et al.

It is certified that error appears in the above-identified patent and that said Letters Patent is hereby corrected as shown below:

Title page,
Item [*] Notice, should read:
-- Subject to any disclaimers, the term of this patent is extended or adjusted under 35 U.S.C. 154(b) by 0 days. --

Signed and Sealed this

Ninth Day of November, 2004

JON W. DUDAS
*Director of the United States Patent and Trademark Office*

Disclaimer

6,774,137 B2—Marcia Johanna Adam, Gisikon (CH); Andrea Fetz, Wetzikon (CH); Gyorgy Lajos Kis, Triboltingen (CH). OPHTHALMIC COMPOSITION. Patent dated Aug. 10, 2004. Disclaimer filed May 25, 2005 by Assignee, Novartis Corp.

Hereby enters this disclaimer to claims 1-13 of said patent.

*(Official Gazette, September 20, 2005)*

UNITED STATES PATENT AND TRADEMARK OFFICE
CERTIFICATE OF CORRECTION

PATENT NO. : 6,774,137 B2 Page 1 of 1
APPLICATION NO. : 10/134795
DATED : August 10, 2004
INVENTOR(S) : Adam et al.

It is certified that error appears in the above-identified patent and that said Letters Patent is hereby corrected as shown below:

On the cover page, directly below the paragraph to the right of (*) Notice:, insert the following:

--This patent is subject to Terminal Disclaimers--.

Signed and Sealed this

Eighth Day of July, 2008

JON W. DUDAS
*Director of the United States Patent and Trademark Office*